(12) United States Patent
Sørensen et al.

(10) Patent No.: US 11,712,151 B2
(45) Date of Patent: Aug. 1, 2023

(54) TIP PART FOR A VISION DEVICE

(71) Applicant: AMBU A/S, Ballerup (DK)

(72) Inventors: Morten Sørensen, Ballerup (DK); Finn Sonnenborg, Frederikssund (DK); Thomas Bachgaard Jensen, Copenhagen V (DK)

(73) Assignee: AMBU A/S, Ballerup (DK)

( * ) Notice: Subject to any disclaimer, the term of this patent is extended or adjusted under 35 U.S.C. 154(b) by 79 days.

(21) Appl. No.: 16/550,014

(22) Filed: Aug. 23, 2019

(65) Prior Publication Data

US 2020/0060520 A1 Feb. 27, 2020

(30) Foreign Application Priority Data

Aug. 24, 2018 (EP) .................... 18190734

(51) Int. Cl.
*A61B 1/00* (2006.01)
*A61B 1/05* (2006.01)
(Continued)

(52) U.S. Cl.
CPC ........ *A61B 1/00096* (2013.01); *A61B 1/0011* (2013.01); *A61B 1/00089* (2013.01);
(Continued)

(58) Field of Classification Search
CPC ............ A61B 1/00064; A61B 1/00071; A61B 1/0008; A61B 1/00096; A61B 1/05;
(Continued)

(56) References Cited

U.S. PATENT DOCUMENTS

| 4,805,596 A | 2/1989 | Hatori |
| 5,193,525 A | 3/1993 | Silverstein et al. |

(Continued)

FOREIGN PATENT DOCUMENTS

| EP | 0 756 845 | 2/1997 |
| EP | 2429376 B1 | 10/2016 |

(Continued)

OTHER PUBLICATIONS

Extended Search Report in related European Application No. 18190734 dated Feb. 1, 2019.

(Continued)

*Primary Examiner* — Ryan N Henderson
(74) *Attorney, Agent, or Firm* — Faegre Drinker Biddle & Reath LLP

(57) ABSTRACT

A tip part for an endoscope has a vision receptor having a vision sensor for providing an image from received light, a first lens, and a casing, the casing supporting the first lens so that the casing substantially maintains a position of the first lens in relation to the vision sensor; a first light source; an exterior housing; and a light shield positioned between the vision receptor and the first light source so as to prevent ingress of stray light from the first light source into the vision receptor by optically shielding the vision receptor; wherein the casing is formed integrally with the exterior housing so that the casing also substantially maintains the first lens in a position in relation to the exterior housing.

23 Claims, 5 Drawing Sheets

(51) Int. Cl.
*A61B 1/06* (2006.01)
*A61B 1/055* (2006.01)
*A61B 1/07* (2006.01)

(52) U.S. Cl.
CPC ............... *A61B 1/05* (2013.01); *A61B 1/055* (2013.01); *A61B 1/0676* (2013.01); *A61B 1/07* (2013.01)

(58) Field of Classification Search
CPC ..... A61B 1/051; A61B 1/0676; A61B 1/0684; A61B 1/0011; A61B 1/00137; A61B 1/00163; A61B 1/06; A61B 1/0661; A61B 1/07; A61B 1/00089
See application file for complete search history.

(56) References Cited

U.S. PATENT DOCUMENTS

| | | | |
|---|---|---|---|
| 5,718,663 A | 2/1998 | Wulfsberg | |
| 5,879,289 A | 3/1999 | Yarush et al. | |
| 5,993,378 A | 11/1999 | Lemelson | |
| 6,503,196 B1 | 1/2003 | Kehr et al. | |
| 7,442,167 B2 | 10/2008 | Dunki-Jacobs et al. | |
| 7,662,094 B2 | 2/2010 | Iddan | |
| 8,414,480 B2 | 4/2013 | Kendale et al. | |
| 8,485,966 B2 | 7/2013 | Robertson | |
| 8,721,531 B2* | 5/2014 | Ichimura | A61B 1/051 600/129 |
| 8,790,250 B2 | 7/2014 | Petersen et al. | |
| 9,220,400 B2 | 12/2015 | Petersen | |
| 9,521,942 B2 | 12/2016 | Robertson | |
| 9,622,649 B2 | 4/2017 | Lin | |
| 9,854,962 B2 | 1/2018 | McGrail et al. | |
| 10,245,402 B2 | 4/2019 | Daher et al. | |
| 10,321,804 B2 | 6/2019 | Jacobsen et al. | |
| 11,382,490 B2 | 7/2022 | Sørensen | |
| 2003/0227547 A1 | 12/2003 | Iddan | |
| 2004/0064018 A1 | 4/2004 | Dunki-Jacobs et al. | |
| 2004/0158129 A1* | 8/2004 | Okada | A61B 1/05 600/168 |
| 2004/0199052 A1 | 10/2004 | Banik et al. | |
| 2004/0242963 A1 | 12/2004 | Matsumoto et al. | |
| 2005/0203341 A1 | 9/2005 | Welker et al. | |
| 2006/0173242 A1* | 8/2006 | Navok | A61B 1/07 600/133 |
| 2006/0281972 A1 | 12/2006 | Pease et al. | |
| 2008/0242935 A1 | 10/2008 | Inoue | |
| 2009/0054728 A1 | 2/2009 | Trusty | |
| 2009/0177040 A1 | 7/2009 | Lyons et al. | |
| 2009/0209819 A1 | 8/2009 | Kitagawa et al. | |
| 2010/0210905 A1* | 8/2010 | Takeuchi | A61B 1/00135 600/110 |
| 2010/0286475 A1 | 11/2010 | Robertson | |
| 2011/0092769 A1* | 4/2011 | Kokubo | A61B 1/128 600/109 |
| 2011/0118549 A1 | 5/2011 | Han | |
| 2011/0245617 A1 | 10/2011 | Kitano | |
| 2012/0065469 A1 | 3/2012 | Allyn et al. | |
| 2012/0209072 A1* | 8/2012 | Oue | A61B 1/00091 600/129 |
| 2012/0323078 A1 | 12/2012 | Kikumori et al. | |
| 2013/0131447 A1 | 5/2013 | Benning et al. | |
| 2013/0172674 A1* | 7/2013 | Kennedy, II | A61B 1/00195 600/109 |
| 2013/0175720 A1 | 7/2013 | Otsuka et al. | |
| 2013/0242071 A1* | 9/2013 | Wada | G02B 23/2484 348/76 |
| 2013/0271588 A1 | 10/2013 | Kirma et al. | |
| 2013/0301149 A1* | 11/2013 | Breidenthal | G02B 23/2476 359/819 |
| 2014/0081085 A1 | 3/2014 | Takato et al. | |
| 2014/0142384 A1* | 5/2014 | Chung | A61B 1/005 600/117 |
| 2015/0150441 A1* | 6/2015 | Ouyang | A61B 10/04 600/109 |
| 2015/0245763 A1* | 9/2015 | Kido | A61B 1/051 600/109 |
| 2015/0335227 A1 | 11/2015 | Jacobsen et al. | |
| 2015/0351620 A1 | 12/2015 | Ruppersberg et al. | |
| 2016/0106306 A1 | 4/2016 | Furuta | |
| 2016/0174819 A1* | 6/2016 | Ouyang | A61B 1/00098 600/105 |
| 2016/0374544 A1 | 12/2016 | Kirma et al. | |
| 2017/0188795 A1* | 7/2017 | Ouyang | G02B 23/2484 |
| 2017/0245734 A1* | 8/2017 | Kaneko | A61B 1/00096 |
| 2017/0310890 A1 | 10/2017 | Wan et al. | |
| 2017/0325663 A1 | 11/2017 | Levy et al. | |
| 2018/0028053 A1 | 2/2018 | Kirma et al. | |
| 2018/0132700 A1 | 5/2018 | Ouyang et al. | |
| 2018/0143421 A1 | 5/2018 | Hegenbarth et al. | |
| 2018/0310890 A1 | 11/2018 | Li | |
| 2019/0175007 A1 | 6/2019 | Sørensen et al. | |
| 2019/0254504 A1 | 8/2019 | Ide | |
| 2019/0282070 A1 | 9/2019 | Sørensen et al. | |
| 2020/0060521 A1 | 2/2020 | Srensen | |
| 2020/0178779 A1* | 6/2020 | Komoro | A61B 1/05 |
| 2020/0288953 A1 | 9/2020 | Qvist et al. | |
| 2020/0297193 A1* | 9/2020 | Takahashi | G02B 7/021 |
| 2020/0405137 A1 | 12/2020 | Qvist et al. | |

FOREIGN PATENT DOCUMENTS

| | | |
|---|---|---|
| JP | H03264037 A | 11/1991 |
| JP | H 032640374 | 11/1991 |
| JP | 2004016455 | 1/2004 |
| JP | 3764512 | 4/2006 |
| JP | 2009-125528 | 6/2009 |
| JP | 2010169802 | 8/2010 |
| JP | 2013009896 | 1/2013 |
| JP | 2018-015250 | 2/2018 |
| JP | 2018015250 | 2/2018 |
| WO | WO 2005/023099 | 3/2005 |
| WO | WO 2008/115575 | 9/2008 |
| WO | WO 2010/066789 | 6/2010 |
| WO | WO 2010/129324 | 11/2010 |
| WO | 2016/188538 A1 | 12/2016 |
| WO | 2016/188542 A1 | 12/2016 |
| WO | WO 2016/188537 | 12/2016 |
| WO | WO 2016/188539 | 12/2016 |
| WO | WO 2016/188540 | 12/2016 |
| WO | WO 2016/188541 | 12/2016 |

OTHER PUBLICATIONS

Extended search report in European application No. 19193599, dated Nov. 11, 2019.
European Search Report in EP 18190736, dated Feb. 11, 2019.
Extended Search Report in European Application No. 18190733.8, dated Feb. 1, 2019.

* cited by examiner

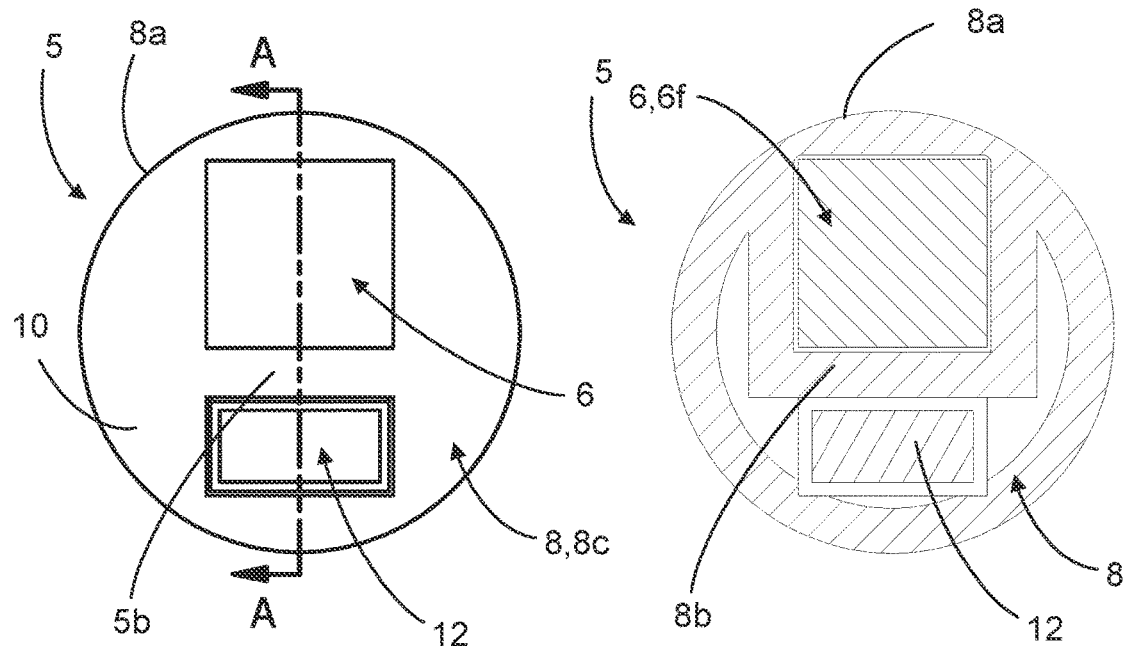
Fig. 2a
Fig. 2c
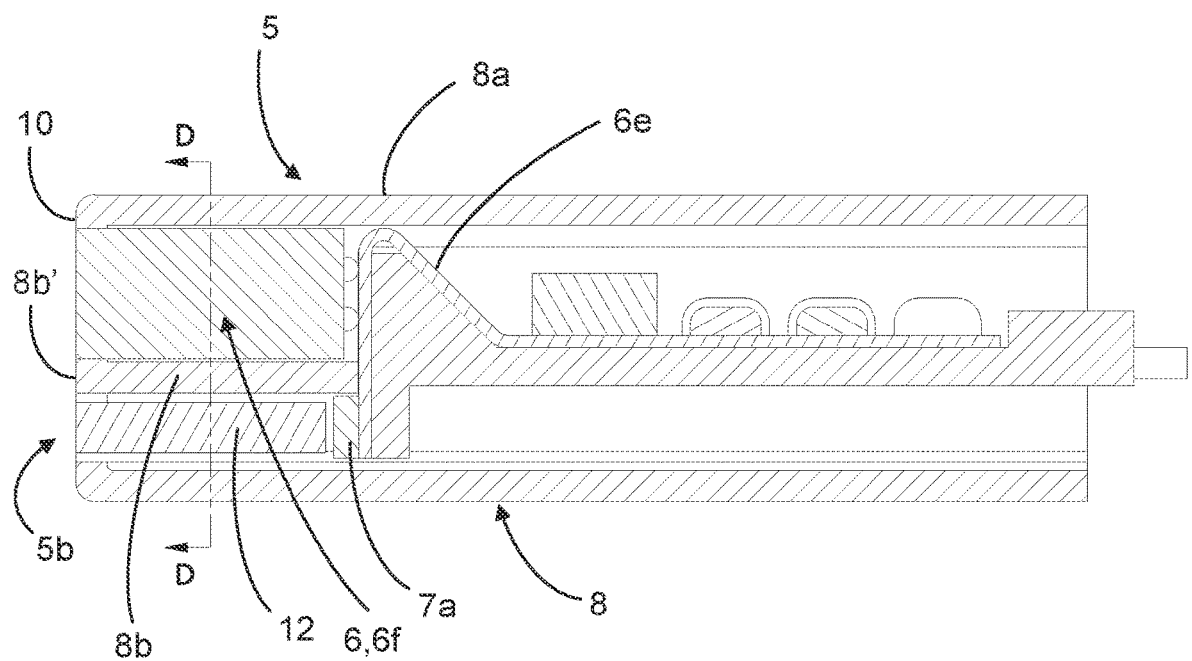
Fig. 2b

TIP PART FOR A VISION DEVICE

CROSS-REFERENCE TO RELATED APPLICATIONS

This application claims priority from European Patent Application No. 18190734, filed on Aug. 24, 2018, which application is incorporated herein by reference thereto.

FIELD OF THE DISCLOSURE

The present disclosure relates to vision devices such as, but not limited to, endotracheal tubes and endoscopes, more specifically to a tip part of such a vision device and a vision device such as an endoscope with such a tip part.

BACKGROUND

Vision devices such as endoscopes are well known for visually inspecting inaccessible places such as human body cavities. Typically, the endoscope comprises an elongated insertion tube with a handle at the proximal end, as seen from the operator, and visual inspection means, such as a built-in camera, at the distal end of the elongated insertion tube. This definition of the terms distal and proximal, i.e. proximal being the end closest to the operator and distal being the end remote from the operator, as used herein for endoscopes in general, is adhered to in the present specification. Electrical wiring for the camera and other electronics, such as LED lighting accommodated in the tip part at the distal end, run along the inside of the elongated insertion tube from the handle to the tip part. Instead of using cameras, endoscopes may also be fibre-optic, in which case the optical fibres run along the inside of the elongated insertion tube to the tip part. A working or suction channel may run along the inside of the insertion tube from the handle to the tip part, e.g. allowing liquid to be removed from the body cavity or allowing for insertion of surgical instruments or the like, into the body cavity. The suction channel may be connected to a suction connector, typically positioned at a handle at the proximal end of the insertion tube.

In order to be able to manoeuvre the endoscope inside the body cavity, the distal end of the endoscope may comprise a bending section with increased flexibility, e.g. a number of articulated segments of which the tip part forms the distalmost segment. The manoeuvring of the endoscope inside the body is typically done by tensioning or slacking pull wires also running along the inside of the elongated insertion tube from the tip part through the remainder of articulated segments to a control mechanism of the handle.

As the name indicates, endoscopes are used for seeing inside things, such as lungs or other human body cavities of a patient. Modern endoscopes are therefore typically equipped with a light source and a vision receptor including a vision sensor, such as a camera or an image sensor. Provided that sufficient light is present, it is possible for the operator to see where the endoscope is steered and to set the target of interest once the tip has been advanced thereto. This therefore normally requires illumination of the area in front of the distal tip of the endoscope, in particular the field of vision of the camera(s). The light source, such as a light emitting diode or an optical fibre, may provide illumination.

The illumination from the light source may result in an undesirable distribution of light, such as overexposure of the sides of the field of vision and underexposure of the centre of the field of vision, leading to poor vision quality.

A portion of light emitted from the light source may ingress into the vision sensor without being reflected by an outside object to be investigated. This type of light may be known as stray light. Stray light may cause unwanted optical artefacts in the image produced by the vision sensor and may generally reduce the quality of an image produced by the vision sensor.

One drawback is that prior art tip parts for endoscopes are generally limited to a fixed set of applications. In some new contemplated applications, investigating narrow and hard-to-reach body cavities are necessary. This requires a miniaturisation of the tip part.

Additionally, when, as in the present disclosure, the tip part is also intended for use in a disposable endoscope, reducing the manufacturing and assembly costs of the tip part are important.

Additionally, when, as in the present disclosure, the insertion tube of the endoscope is intended to be inserted into a human body cavity, the insertion tube furthermore needs to be sealed in a watertight manner. This is in particular the case for the distal tip part as it accommodates the camera, LED(s) and other delicate electronics, prone to malfunction or destruction if exposed to humidity.

On this background, it may be seen as an object of the present disclosure to provide a tip part mitigating at least some of the above drawbacks.

One or more of these objects may be met by the present disclosure as described in the following.

SUMMARY OF THE DISCLOSURE

A tip part for an endoscope and an endoscope including the tip part are provided. A first aspect of the present disclosure relates to a tip part for an endoscope. In some embodiments, the tip part comprises a vision receptor having a vision sensor for providing an image from received light, a first lens, and a casing, the casing supporting the first lens so that the casing substantially maintains a position of the first lens in relation to another lens and/or in relation to the vision sensor; a first light source; an exterior housing accommodating the vision receptor and the first light source; a proximal or back end for connection to other parts of the vision device, such as an insertion tube of an endoscope; a distal or front end for receiving light received from the object; and a light shield positioned between the vision receptor and the first light source so as to prevent ingress of stray light from the first light source into the vision receptor by optically shielding the vision receptor; wherein the casing is formed integrally with the exterior housing so that the casing also substantially maintains the first lens in a position in relation to the exterior housing.

This may provide the advantage that the tip part can be miniaturised as a separate lens barrel is dispensed with. This may enable a number of different applications for the tip part. For instance, an endoscope with such a tip part may be used to investigate more narrow and hard to reach cavities of the human body. The assembly of the tip part may be made simpler as fewer parts have to be assembled. Additionally, the position of the lens or lenses in relation to the exterior housing and/or window may be controlled more precisely as the casing holding the lens or lenses are fixed in relation to the exterior housing. A tip part of this kind may also increase the vision quality of the vision sensor as stray light ingressing into the vision receptor is reduced.

Additionally or alternatively, the casing may support the vision sensor so that the casing substantially maintains a position of the vision sensor in relation to the first lens and/or in relation to another lens. The casing may at least partially surround or enclose the first lens, and/or another lens, and/or the vision sensor. The casing may fix the position of the first lens, and/or another lens, and/or the vision sensor in relation to each other. The casing may extend along a side or an optical axis of the first lens or lenses.

Additionally, the vision receptor may comprise a lens barrel supported by the casing so that the casing substantially maintains a position of the vision sensor in relation to the first lens and/or in relation to another lens. The casing may at least partially surround or enclose the lens barrel, the first lens, and/or another lens, and/or the vision sensor. The casing may fix the position of the lens barrel, the first lens, and/or another lens, and/or the vision sensor in relation to each other. The lens barrel and the casing may extend along a side or an optical axis of the first lens or lenses. Use of a lens barrel may facilitate low-cost assembly of the tip part.

The vision sensor of the vision receptor may be an image sensor. The vision receptor may comprise a lens or a plurality of lenses potentially arranged successively and optionally in the casing. The plurality of lenses may be arranged in front of the vision sensor, potentially so that an optical axis of the lens, potentially of the plurality of lenses, align or coincide with an optical axis of the vision sensor. The plurality of lenses may be spaced by at least one spacer, potentially a plurality of spacers. The vision receptor may comprise a printed circuit board for converting light received by the vision receptor to an image. The exterior housing may accommodate the printed circuit board.

The exterior housing may further comprise an exterior side wall. The exterior side wall may extend from the distal end of the tip part to the proximal end of the tip part. The exterior side wall may extend from the window. The exterior side wall may extend along sides of the vision receptor and first light source. The exterior side wall may have a substantially cylindrical shell shape. The exterior side wall and window may be integrally formed. The exterior housing, potentially the exterior side wall of the exterior housing, may form a barrier or border between the exterior of the tip part and the interior of the tip part. The exterior housing may define an internal volume, in which the vision receptor and the light source are positioned. The exterior housing may accommodate a working channel for supplying fluid to the distal end of the tip part, a printed circuit board of the vision receptor, and/or a vision sensor of the vision receptor.

The tip part may comprise a working tube potentially forming part of the working channel of the endoscope. The exterior housing may accommodate the working tube. The working tube may be sealed in relation to the exterior housing, potentially so that fluid in the working tube may not ingress into the interior of the exterior housing.

Additionally or alternatively, the light source or light source(s) may be a light fibre(s) and/or light emitting diode(s).

The first lens may form part of a plurality of lenses arranged successively in the casing. The first lens or the plurality of lenses may be chosen to provide suitable optical characteristics for the vision sensor. The type of the first lens or the plurality of lenses may be selected from the group consisting of: plano-concave, plano-convex, bi-concave, bi-convex, positive meniscus, negative meniscus, fresnel, wafer, or any other suitable lens type.

The tip part may comprise a second light source. The second light source may be provided similarly as the first light source. The second light source may be positioned on an opposite side of the vision receptor in relation to the first light source.

The window may have different shapes, such as circular, half-moon shaped. The window may comprise a plurality of window elements. The window elements may abut each other. The window elements may be fixed to each other, potentially by gluing or welding. The window may preferably be integrally formed in one piece.

Additionally or alternatively, the window may be a front window, potentially allowing the vision receptor to receive image information from the front of the tip part. The exterior surface of the window may be an exterior front surface.

Additionally or alternatively, the window may be a side window, for instance when the endoscope is a duodenum endoscope. The side window may allow the vision receptor to receive image information from a side, potentially from a radial direction, of the tip part. The exterior surface of the window may be an exterior side surface.

Additionally or alternatively, the window may comprise a front window and a side window.

Additionally or alternatively, the light shield may consist essentially of a light shielding material. The light shielding material may be a substantially opaque, and potentially black, material. The light shielding material may be an opaque polymer.

In this specification, stray light may be defined as light emitted from a light source, which ingresses into a vision receptor before being reflected by an outside or investigated object, for instance by internal reflections in the window. This may cause unwanted optical artefacts in the image produced by the vision receptor.

In this specification, a lens may be defined as a device with curved surfaces having the ability to focus, collimate, or disperse light propagating through curved surfaces of the lens.

In this specification, the term "in front of" when referring to the position of an element relative to an optical device, such as a lens, a vision receptor, and/or a light source, the element may be understood to be positioned so that the optical device has an optical effect on the element. For instance, a lens positioned in front of a light source may be understood so that the lens is positioned so that light emitted from the light source propagates directly through the lens.

In this specification, the term "to accommodate" may additionally or alternatively be defined as "to house" or "to enclose" or "to surround". For instance, the exterior housing may enclose or surround the vision receptor and/or the light source.

In this specification, the terms "integrally" or "integrally provided" or "integrally comprising" or similar may be defined as the associated features forms an integral part of a whole; and/or be moulded in one piece; and/or be substantially inseparable by hand.

In this specification, the term "proximal" may be defined as being closest to the operator and the term "distal" as being remote from the operator. The term "proximal-distal axis" may be defined as an axis extending between these two extremes, in the present case the proximal-distal axis may be a centre axis of the tip part extending between a proximal extremity of the proximal end of the tip part and a distal extremity of the distal end of the tip part. A front part of the tip part may be distally oriented and a back or rear part of the tip part may be proximally oriented.

In this specification, the distal end of the tip part should not be construed to only comprise the most distal extremity of the tip part, rather the term "distal end of the tip part"

should be understood as a portion of the tip part being distally positioned, e.g. a remaining portion of the tip part relative to the proximal or back end and/or a portion of the tip part for not being connected to other parts of the endoscope and/or a distally located half of the tip part. In some embodiments, the window may be a side window positioned at the distal or front end of the tip part.

In this specification, the term "interior" may be defined as being positioned in an interior space of the tip part, and the term "exterior" may be defined as being positioned in an exterior space of the tip part or as not being positioned in an interior space of the tip part.

In this specification, an endoscope may be defined as a device adapted for viewing bodily cavities and/or channels of a human and/or animal body. The endoscope may for instance be a conventional flexible or steerable endoscope or a rigid endoscope or an endotracheal tube potentially provided with a camera and light source for ensuring the correct position of the endotracheal tube, for instance a laryngoscope. The endoscope may be a duodenum endoscope.

The tip part may alternatively be for a medical vision device, such as an endoscope.

Additionally or alternatively, the casing and/or the light shield may at least partially surround(s) the vision receptor.

This may provide the advantage of reducing the amount of stray light ingressing into the vision receptor.

Additionally or alternatively, the casing and/or the light shield may at least partially surround(s) or encase(s) or enclose(s) the vision receptor, potentially the first lens or the plurality of lenses or the vision sensor. The casing and the light shield may at least partially enclose the first lens and the vision sensor.

Additionally or alternatively, the casing and/or light shield is/are U-shaped, potentially so as to at least partially encase the vision receptor.

Additionally or alternatively, the light shield may be separate from the casing.

This may provide the advantage that the properties of the light shield may be chosen more independently of the properties of the casing, for instance the material of the light shield.

The light shield may be provided as a cover for the casing. The cover may comprise a sleeve slidable over the casing. The sleeve may be made from an opaque layer of material including polymers, paper and the like.

Additionally or alternatively, the light shield may be a light shielding layer provided on the casing.

Additionally or alternatively, the light shield may be comprised by the casing, by forming the casing from an opaque material.

This may provide a particularly simple way of providing the light shield.

The light shielding layer may consist essentially of a substantially opaque, and potentially black, material. The light shielding layer may be provided as an at least partial cladding or coating on the casing. The light shielding layer may be provided as a hardened opaque glue on the casing. Such a light shielding layer may enable use of a transparent exterior housing and casing. The light shielding layer may be provided as a hardened opaque glue on the inside of the casing, which glue may affix a lens barrel.

Additionally or alternatively, the casing and the light shield may be integrally formed or be in one piece.

This may provide a particularly simple way of manufacturing the tip part.

The exterior housing and the casing may essentially consist of the light shielding material. The exterior housing and the casing may be formed as a one-piece part by a two component moulding process, so that the casing consists essentially of the light shielding material and the exterior housing consists essentially of a different material.

Additionally or alternatively, the exterior housing may comprise an exterior surface positioned at the distal end of the tip part, wherein a distal end of the light shield may be arranged substantially flush with the exterior surface. The exterior surface may be the surface of a front wall of the exterior housing.

By having the light shield extend so that it is at least arranged substantially flush with the exterior surface, the amount of stray light potentially ingressing into the vision receptor may be reduced, thus improving the image quality provided by the vision receptor.

The light shield may form an integral part of the casing, so that a distal end of the casing is arranged substantially flush with the exterior surface. Additionally or alternatively, the distal end of the light shield may extend further distally than the exterior surface. The distal end of the light shield and/or casing may form part of the exterior surface of the exterior housing.

Additionally or alternatively, a distal end of the casing and/or the light shield extend(s) through the window so as to be positioned at least substantially flush with, potentially further distal than, the exterior surface of the exterior housing or of the window.

Additionally or alternatively, a distal end of the casing and/or the light shield may be positioned substantially flush with the substantially planar exterior surface of the window.

Additionally or alternatively, the casing and/or light shield may comprise a distal segment positioned at a distal end of the casing. The distal segment may be embedded in the window. This may provide the advantage that the distal segment prevents internal reflections in the window from reaching the vision receptor.

Additionally or alternatively, the exterior housing may comprise a window comprising the exterior surface and being positioned at the distal end of the tip part, the window consisting essentially, potentially being of, a transparent material so that light received from the object can pass through the window to the vision receptor, and so that light emitted from the first light source can pass through the window to the exterior, the exterior surface being positioned at least partly in front of the vision receptor and the first light source.

Additionally or alternatively, the exterior housing integrally comprises the window. Additionally or alternatively, the window forms part of the exterior housing.

The window may comprise, potentially consist essentially of, a transparent material. A transparent material will be able to transmit some image information and may potentially be defined as allowing at least 50% of light entering the window at the exterior surface to pass through the window. A transparent material will be able to transmit more image detail than a translucent material. The transparent material may be a polymer, glass, plastic polymer, or any other suitable material, e.g. silicone.

Additionally or alternatively, the transparent material is different from the material of the light shield.

Additionally or alternatively, the window may comprise a first light source zone able to transmit light emitted from the first light source to outside of the tip part. The first light source zone may comprise a substantially planar first light reception end facing the first light source.

Additionally or alternatively, the first light source zone may be positioned between the exterior surface and the first light source. The first light source zone may have no lens effect.

Additionally or alternatively, the window may comprise a vision receptor zone able to transmit light received from outside the window to the vision receptor, the vision receptor zone potentially comprises a substantially planar abutment surface facing the front of the vision receptor.

Additionally or alternatively, the vision receptor zone potentially may be positioned between the exterior surface and the vision receptor. The vision receptor zone may have no lens effect.

Additionally or alternatively, the exterior surface may be substantially planar, and/or potentially having no lens effect.

Additionally or alternatively, the exterior housing may comprise a side wall extending from the window along sides of the vision receptor and the first light source, the side wall and window being integrally formed or being in one piece.

Additionally or alternatively, the window may comprise, potentially consists essentially of, a first material and the exterior housing may comprise, potentially consists essentially of, a second, different material, the window and exterior housing being integrally formed potentially by a two component moulding process.

Additionally or alternatively, first lens or the plurality of lenses may be is a wafer lens or wafer lenses.

This may be advantageous since wafer lenses may be provided in an unshielded wafer stack.

Additionally or alternatively, the vision receptor may comprise a lens stack having the first lens and a second lens, the lens stack being positioned inside the casing, the second lens being positioned successively in front of the first lens.

Additionally or alternatively, the lens stack may comprise at least one lens spacer positioned between the first and the second lens.

Additionally or alternatively, the casing may abut the vision sensor and the first lens.

Additionally or alternatively, the casing is in direct contact with the vision receptor and/or the first lens.

Additionally or alternatively, the vision receptor and/or tip part does not comprise a separate, and potentially opaque, lens barrel or envelope configured to support the first lens or plurality of lenses.

Additionally or alternatively, an endoscope may comprise a tip part according to the first aspect of the present disclosure. The endoscope may comprise an elongated insertion tube with a handle at the proximal end. The tip part may be positioned at the distal end of the elongated insertion tube. The tip part may further comprise a bending section positioned between the tip part and the elongated insertion tube. The bending section may be configured to articulated, so as to manoeuvre the endoscope inside a body cavity. Brief description of drawings

BRIEF DESCRIPTION OF THE DRAWINGS

The present disclosure will now be described in greater detail based on non-limiting exemplary embodiments and with reference to the drawings, on which:

FIG. 2a shows a front view of a distal end of the tip part of FIG. 1b, FIG. 2b shows a cross-sectional view of the tip part along the line A-A of FIG. 2a, FIG. 2c shows a cross-sectional view of the tip part along the line D-D of FIG. 2b, FIG. 5b shows a cross-sectional view of the tip part along the line E-E of FIG. 4a.

DETAILED DESCRIPTION OF THE DRAWINGS

Figure 1A:
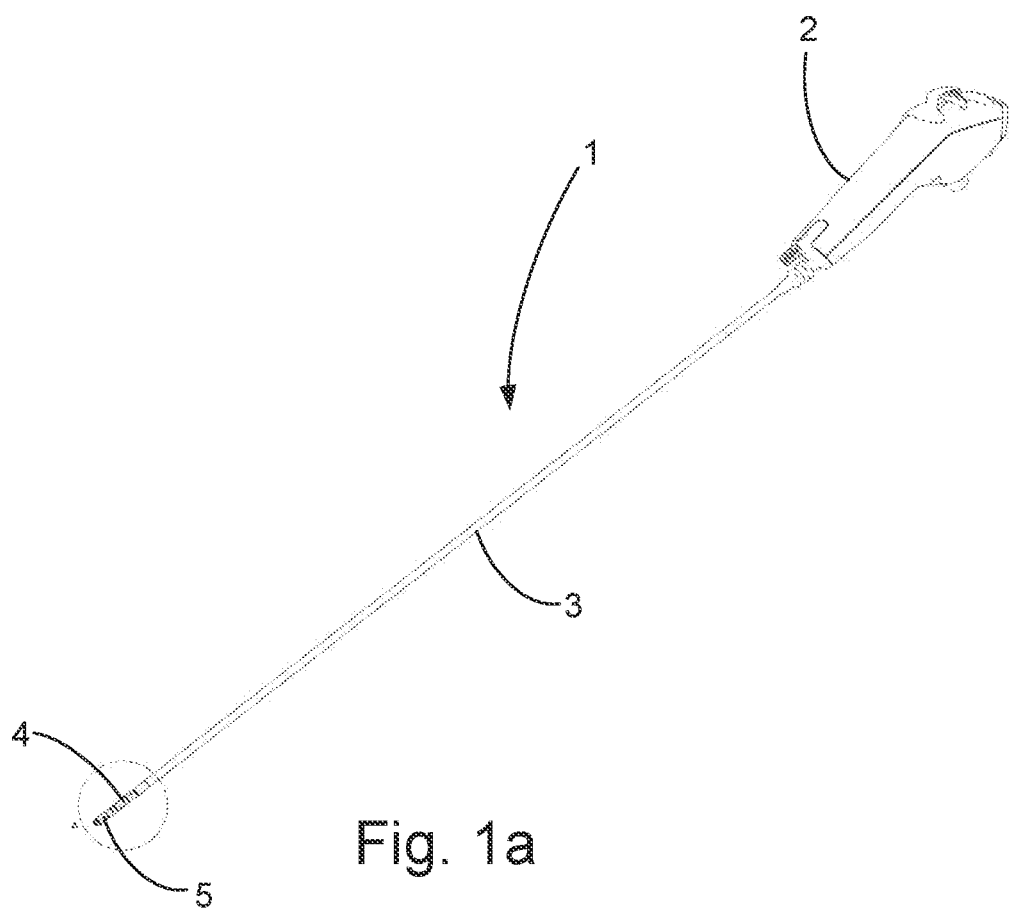
FIG. 1a shows a perspective view of an endoscope in which a tip part according to the present disclosure is implemented.

Turning first to FIG. 1a, an endoscope 1 exemplifying the vision device according to the present disclosure is shown. The endoscope 1 comprises a handle 2 at the proximal end of the endoscope 1, an insertion tube 3 extending towards the distal end of the endoscope 1 where it comprises an articulated bending section 4, which as the most distal segment has a distal tip part 5 according to the present disclosure. Though omitted for illustration purposes the articulated bending section 4 will normally be covered by a suitable sleeve, connected at least at its own distal end to the distal tip part 5, e.g. by means of an adhesive. The tip part 5 of the present disclosure is intended as a tip part 5 for a disposable endoscope 1 to be thrown away after use and low manufacturing costs is therefore an important issue.

Figure 1B:
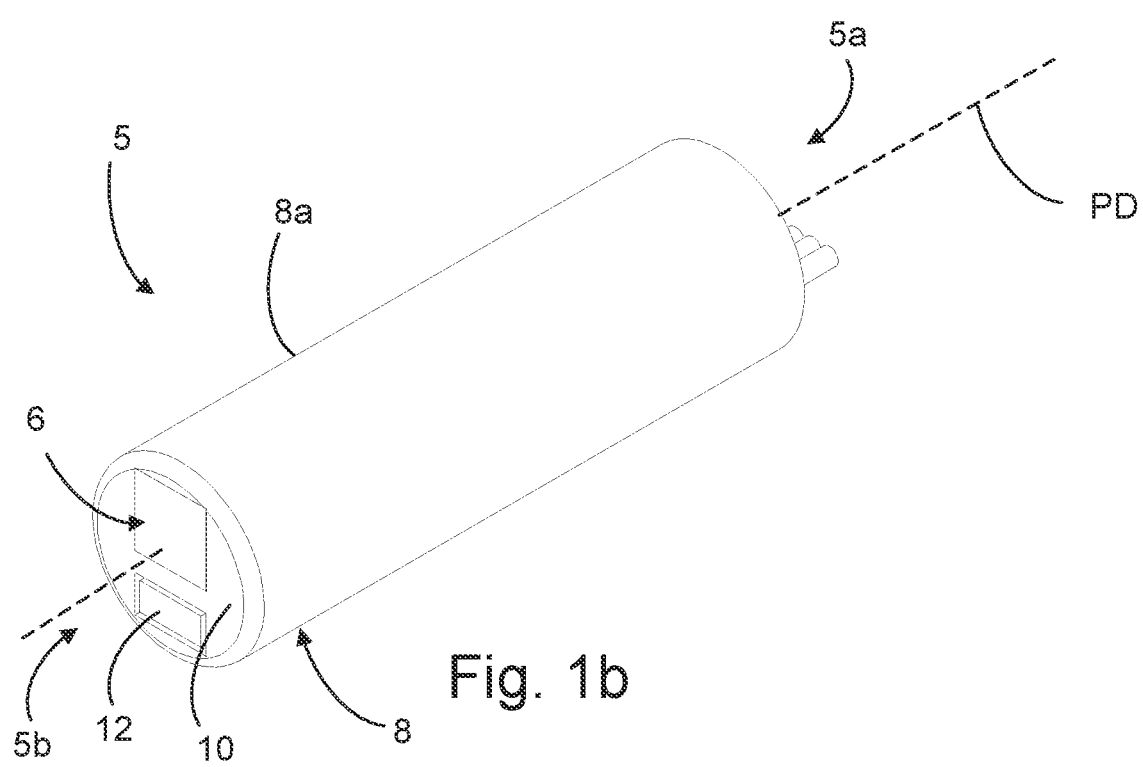
FIG. 1b shows a perspective view of a first embodiment of a tip part according to the present disclosure.

FIG. 1b shows a first detailed embodiment of a tip part 5 configured to be incorporated in the endoscope shown in FIG. 1a. The tip part 5 has a proximal end 5a for connection to the insertion tube 3 of endoscope 1 and a distal end 5b for receiving light from an object (not shown) located in front of the tip part. The tip part 5 further comprises an exterior housing 8 including a front wall 8c having an exterior surface 10 positioned at the distal end 5b of the tip part 5, and an exterior side wall 8a extending from the front wall 8c along a proximal-distal axis PD of the tip part. The wall 8a and exterior surface 10 are integrally formed in one piece. The exterior housing 8 forms a barrier between the exterior of the tip part 5 and the interior of tip part 5. The exterior side wall 8a has a substantially cylindrical shell shape.

FIG. 2a shows the position of a first cross-sectional line A-A on the first embodiment of the tip part 5 of FIG. 1b.

Turning to FIG. 2b showing cross section A-A, the tip part 5 comprises a vision receptor 6 having a vision sensor (not shown) for providing an image from received light, a first lens (not shown), a printed circuit board 6e configured for processing the image, and a casing 8b. The casing 8b supports the first lens and maintains a position of the first lens in relation to another lens (not shown) and in relation to the vision sensor. The tip part 5 further comprises a first light source 7a, in the form of a light emitting diode, positioned behind a light guide 12. The light guide 12 may be arranged in a tube of the exterior housing and sealed to the exterior housing 8 by hardened glue. The tube forms a tubular cavity for the light guide and may be molded in one piece with the casing and the exterior housing, projecting inwardly from the front wall 8c of the exterior housing. Alternatively, the light guide 12 may be bonded to the bottom of the casing.

Figure 4A:
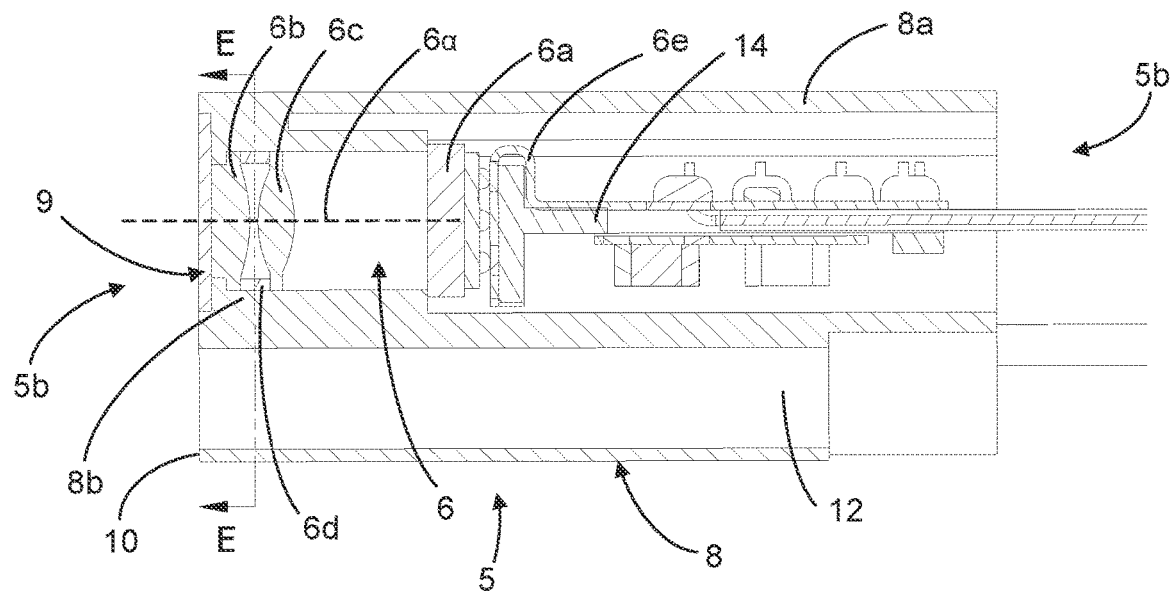
Figure 4B:
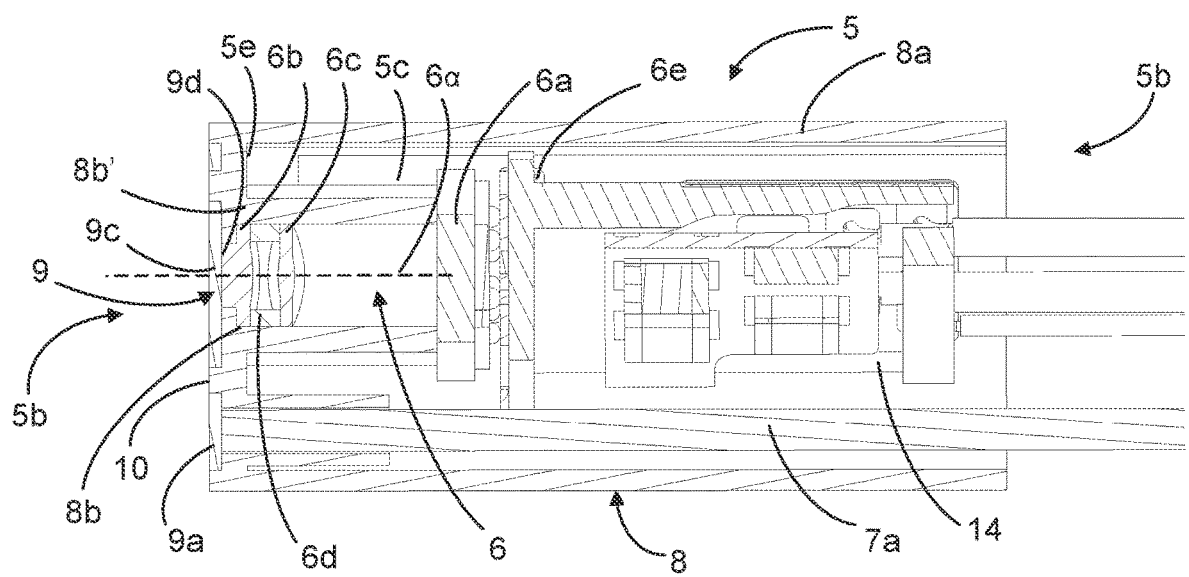

Alternatively, the light guide 12 may be formed in a one-piece construct with the exterior housing. Reducing the number of parts reduces the cost of the single-use tip part by reducing assembly labor costs. Additionally, the one-piece construct eliminates the need to bond the light guide 12 to the tube or the exterior housing. The exterior housing 8 accommodates and surrounds the vision receptor 6 and the first light source 7a. The casing 8b is positioned between the vision receptor 6 and the first light source 7a and may be made of an opaque light shielding material so as to prevent ingress of stray light from the first light source 7a into the vision receptor 6 by optically shielding the vision receptor 6. A small gap between the lens barrel 6f of the vision receptor 6 and the casing 8b is filled with hardened glue preventing the vision receptor 6 from sliding in relation to the casing 8b and providing water tightness so as to seal off the printed circuit board 6e and other electronics in the tip part 5. The hardened glue may also perform the light shielding function, e.g. opaque glue. In one variation, the casing 8b and the exterior housing 8 are molded in one-piece. In another variation, the casing 8b, the exterior housing 8, and the light guide 12 are molded in one-piece. In variations including the lens barrel 6f, the vision receptor 6 may be attached to the printed circuit board 6e via the electrical connections of the vision sensor 6a and then inserted from the rear into the casing 8b, where it is bonded in place via the adhesive. The vision receptor 6/printed circuit board 6e assembly may be inserted forward until the circuit board 6e abuts the casing 8b. The lens 6b and the vision sensor 6a (not shown) may be fit into the lens barrel 6f to form the vision receptor 6, wherein the relationship between the lens 6b and the vision sensor 6a is fixed. Internal chamfers or slots may be provided in the lens barrel matching, at least in relevant part, the peripheral shape of the lens and vision sensor. A transparent window (not shown) may be bonded to the casing 8b at the front wall 8c or the lens barrel 6f, sealing the lens and image receptor therein. The window may part of the vision receptor 6. In another examples, the lens barrel is omitted from the vision receptor 6, and the printed circuit board 6e/vision sensor 6a are fit to the proximal end of the casing 8b in the manner previously described. The lens 6b is also fit to the casing 8b, but inserted from the front, therefore the casing 8b fixes the relationship between the lens 6b, and any additional lens, and the vision sensor 6a. Examples of lenses and windows fit to the casing or the front wall of the exterior housing are shown in FIGS. 4a and 4b.

The first light source 7a is similarly connected to the printed circuit board 6e and inserted from the rear into the tubular cavity between the casing 8b and the exterior side wall 8a. In embodiments where the light tube 12 is not integrally formed in one-piece with the exterior housing, the light tube 12 may be inserted in the tubular cavity from the front and bonded to exterior housing or the casing.

Turning to FIG. 2c, the exterior housing 8 forms a barrier between the exterior of the tip part 5 and the interior of tip part 5. The casing 8b is formed integrally with the exterior housing 8 so that the casing 8b also substantially maintains the first lens in a position in relation to the exterior housing 8. The casing 8b supports the vision sensor of the vision receptor 6 so that the casing 8b maintains and fixes a position of the vision sensor of the vision receptor 6 in relation to the first lens. The casing 8b surrounds and encloses the first lens and the vision sensor of the vision receptor 6.

Figure 3A:
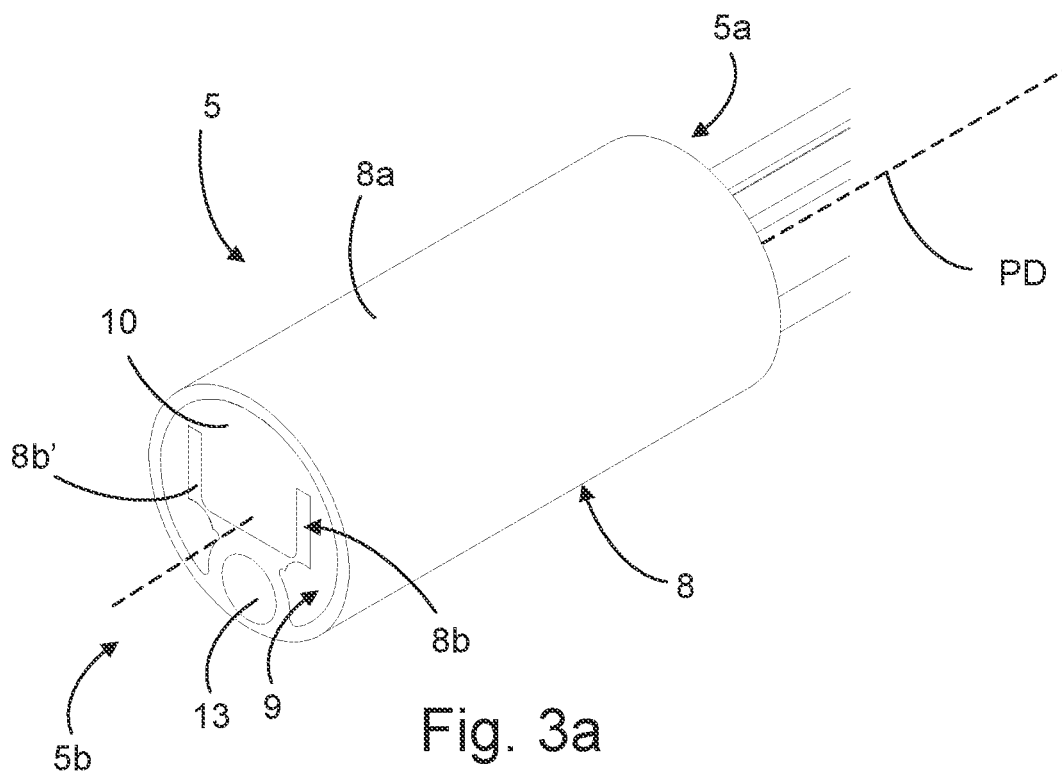
FIG. 3a shows a perspective view of a second embodiment of a tip part according to the present disclosure.

A second embodiment according to the present disclosure is shown in FIG. 3a. In the following, the differences between the first and the second embodiment will be discussed. Reference numerals will be the same for features present in the first and the second embodiment.

The second embodiment of a tip part 5 is, similarly to the first embodiment, configured to be incorporated in the endoscope shown in FIG. 1a.

The tip part 5 includes a window 9 positioned at the distal end 5b. The window 9 and the exterior housing 8 are integrally formed in one piece. A front view of the second embodiment is shown in FIG. 3b.

Figure 3B:
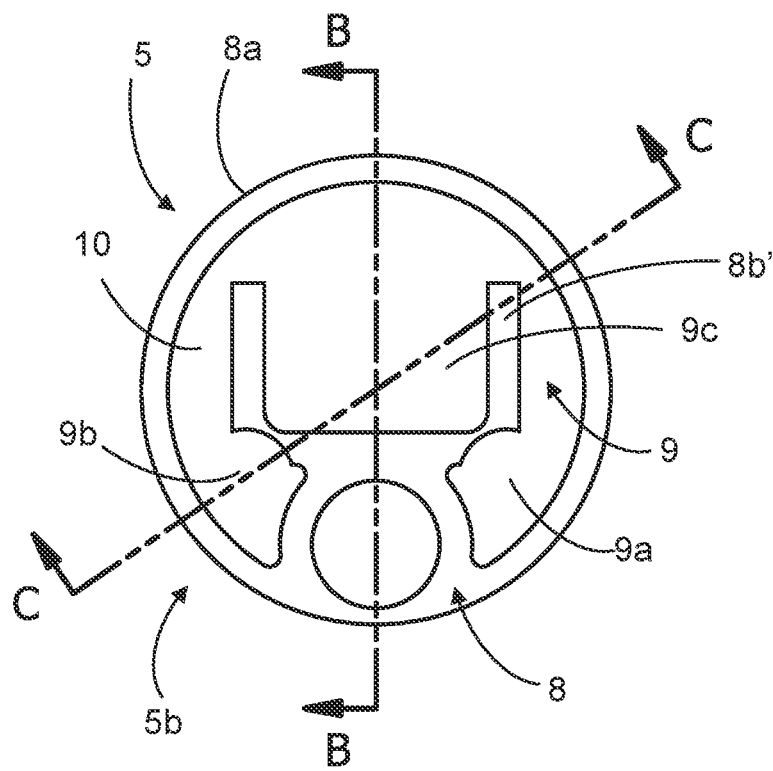
FIG. 3b shows a front view of the second embodiment of FIG. 3a, FIG. 4a shows a cross-sectional view of the tip part with a schematic first and second lens along the line B-B of FIG. 3a, FIG. 4b shows a cross-sectional view of the tip part with a schematic first and second lens along the line C-C of FIG. 3a, FIG. 5a shows a perspective of the tip part without a window according to the second embodiment.

Turning to FIG. 3b showing a front view of the second embodiment, the window 9 comprises a first light source zone 9a and a second light source zone 9b positioned directly in front of the associated light source 7a, 7b (see FIG. 5a) so as to allow light emitted from the light sources 7a, 7b to propagate outside of the tip part 5. Each light source zone 9a, 9b includes a substantially planar light reception end facing the associated light source 7a, 7b. The light source zones 9a, 9b extend from the exterior surface 10 of the window 9 to the associated light reception end.

The window 9 comprises a vision receptor zone 9c positioned directly in front of the first lens 6a of the vision receptor 6 so as to allow light to propagate from an object in front of the tip part 5 through the vision receptor zone 9c to the vision receptor 6. The vision receptor zone 9c includes a substantially planar abutment surface 9d facing the first lens 6a. The vision receptor zone 9c extends from the exterior surface 10 of the window 9 to the abutment surface 9d.

The interior of the second embodiment is shown in FIGS. 4a and 4b. FIG. 4a shows a cross section with mirror symmetry. FIG. 4b shows the interior spacing 5c formed by the front wall 8c and the exterior facing side wall 8a, and the exterior and interior surfaces of the front wall 8c, denoted, respectively, by numerals 10 and 5e.

The tip part 5 comprises a vision receptor 6 configured to provide an image from light received from an object to be investigated, such as a human body cavity. The vision receptor 6 includes a vision sensor 6a for providing an image from received light, a first lens 6b, a second lens 6c, a lens spacer 6d, a printed circuit board 6e for processing the image from the vision sensor, and a casing 8b. The lenses 6b, 6c are arranged successively in the casing. The lens spacer 6d is arranged between the lenses 6b, 6c to ensure that the lenses do not abut each other. The lenses 6b, 6c are arranged in front of the vision sensor 6a. The lenses 6b, 6c are shown with schematic geometry and are chosen according to the requirements of the vision sensor 6a. The vision receptor 6 may be assembled within the exterior housing 8 of the tip part 5 as described above.

The casing 8b is a lens barrel preferably made of an opaque, black material so as to prevent light from ingressing into the vision receptor 6. The casing 8b supports the vision sensor 6a and substantially maintains and fixes the position of the vision sensor 6a in relation to the first lens 6b and to the second lens 6c. The casing 8b extends along a side of the first lens 6b and the second lens 6c, and along an optical axis 6α of the lenses 6b, 6c.

The exterior housing 8 and the casing 8b are integrally formed and essentially consist of a light shielding material in the form of a black, opaque plastic polymer.

The tip part 5 further comprises a first light source 7a and a second light source 7b (see FIG. 5a) each being a light fibre abutting an interior surface of the window 9. The second light source 7b is provided similarly to the first light source 7a but on an opposite side of the vision receptor 6.

The window 9 is made of a transparent rigid polymer material. The window 9 comprises a planar exterior surface positioned directly in front of the vision receptor 6, the first light source 7a, and the second light source 7b, so that light received from the investigated object can pass through the window 9 to the vision sensor 6a of the vision receptor 6, and so that light emitted from the light sources 7a, 7b can pass through the window 9 to the outside of the tip part 5.

The exterior housing 8 and the window 9 are formed by a two component moulding process, so that the exterior housing 8 including the casing 8b consists essentially of the light shielding material and the window consists essentially of the transparent material.

The tip part further comprises an interior housing 14 positioned inside the exterior housing 8. The interior housing 14 does not provide sealing for the internal parts of the tip part 5. The interior housing 14 may provide a simple way of assembling some electronic parts of the tip part 5 prior to final assembly of the tip part.

Figure 5A:
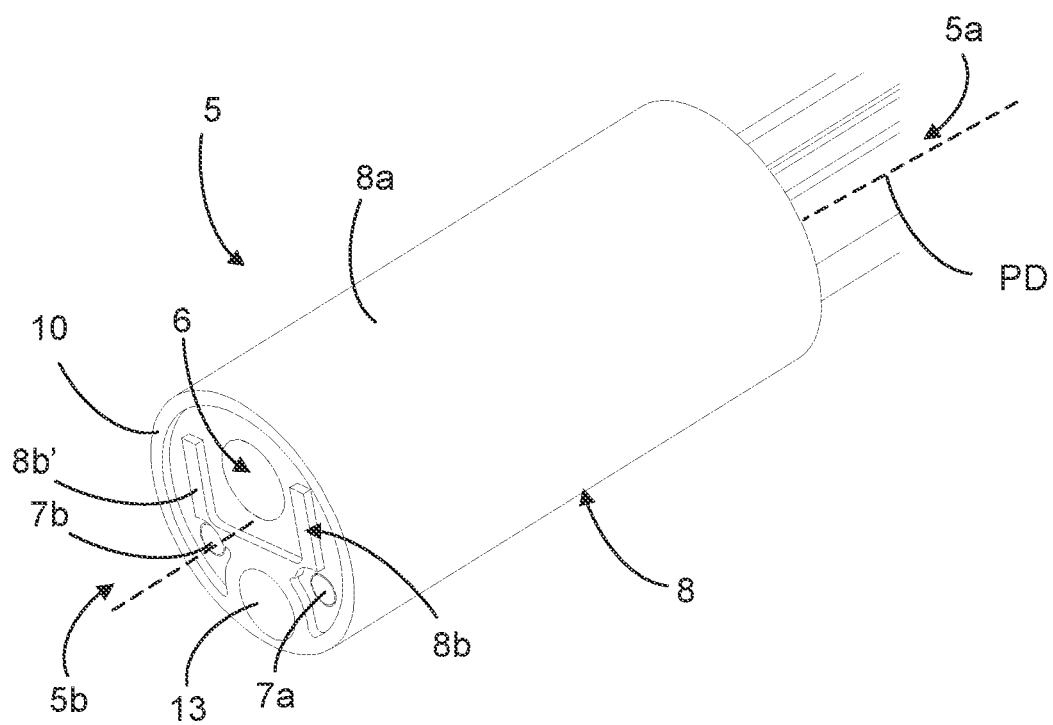

Turning to FIG. 5a, the light shielding casing 8b comprises a distal casing end 8b' positioned at the distal end 5b of the tip part 5. The distal casing end 8b' forms a U-shape positioned between the first light source 7a and the second light source 7b and the vision receptor 6. In particular the distal casing end 8b' is positioned between the first and second light source zones 9a, 9b and the vision receptor zone 9c, as best seen on FIG. 3a. The U-shaped distal casing end 8b' extends through the window 9, as best seen in FIG. 3a, so that it is arranged substantially flush with the exterior surface 10 and forms part of the exterior surface 10. The U-shaped distal casing end 8b' are thus embedded in the window 9, so as to provide a light shield for preventing internal reflections in the window 9 reaching the vision receptor 6.

Figure 5B:
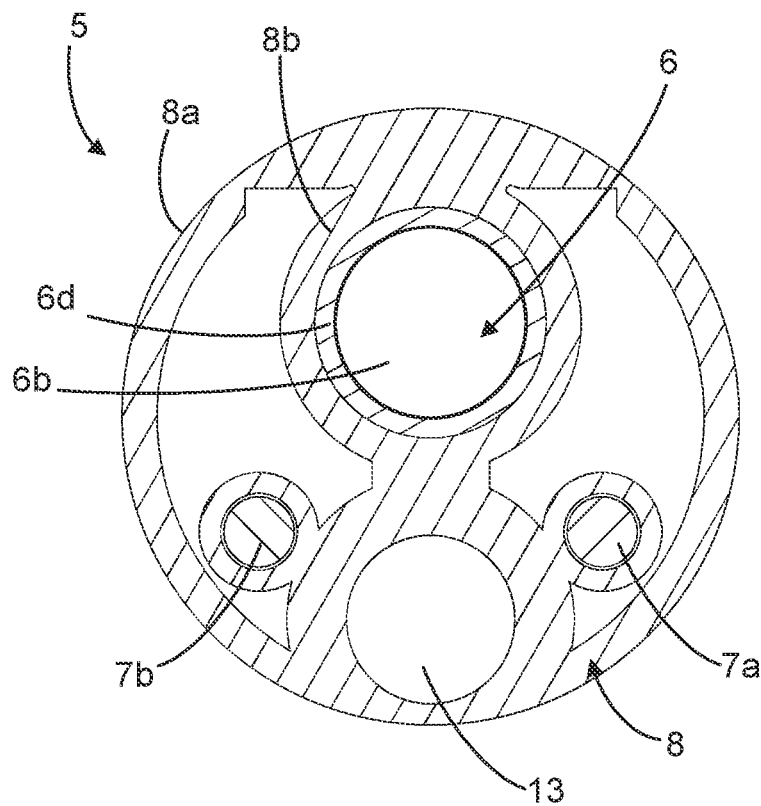

Turning to FIG. 5b, the casing 8b surround and enclose the first lens 6b and the second lens 6c. The casing 8b is made of a light shielding material to provide a light shield between the vision receptor 6 and the light sources 7a, 7b.

LIST OF REFERENCES

The following is a list of reference numerals used throughout this specification.
1 endoscope
2 handle
3 insertion tube
4 bending section
5 tip part
5a proximal end
5b distal end
6 vision receptor
6a vision sensor
6b first lens
6c second lens
6d spacer
6e printed circuit board
6α optical axis of vision receptor
6f lens barrel
7a first light source
7b second light source
8 exterior housing
8a exterior side wall
8b casing
8b' distal end of casing
8c front wall
9 window
9a first light source zone
9b second light source zone
9c vision receptor zone
9d abutment surface
10 exterior surface
11a first optical well
11b second optical well
12 first light guide
13 tube
14 interior housing
PD proximal-distal axis

We claim:

1. A tip part for an endoscope, said tip part comprising:
a vision receptor having a first lens and a vision sensor for providing an image from received light;
a casing with an internal surface supporting and contacting the first lens so that the casing substantially and directly maintains a position of the first lens in relation to another lens and/or in relation to the vision sensor;
a window made of a transparent material and positioned at a distal end of the tip part at least partly in front of the first lens, the window comprising a light source zone and a vision receptor zone;
a first light source;
an exterior housing having a distal or front end longitudinally opposite and spaced apart from a proximal or back end, the exterior housing having an exterior facing side wall extending from the front end to the back end and a front wall connected to the exterior facing side wall at the front end, the front wall and the exterior facing side wall defining an interior spacing, the exterior housing formed in one-piece with the casing and the front wall and accommodating the vision receptor and the first light source in the interior spacing, the front wall having an exterior surface and an interior surface opposite the exterior surface, the casing extending in the interior spacing from the interior surface of the front wall toward the back end; and
a light shield positioned between the vision receptor and the first light source so as to prevent ingress of stray light from the first light source into the vision receptor by optically shielding the vision receptor,
wherein the casing comprises a distal end embedded in the window at least in part between the light source zone and the vision receptor zone to prevent internal reflections in the window from reaching the vision receptor.

2. The tip part of claim 1, wherein the casing is made of an opaque material forming the light shield, which at least partially surrounds the vision receptor.

3. The tip part of claim 1, wherein the light shield is separate from the casing.

4. The tip part of claim 1, wherein the light shield is a light shielding layer provided on the casing.

5. The tip part of claim 1, wherein a distal end of the light shield is arranged substantially flush with the exterior surface of the front wall.

6. The tip part of claim 5, wherein the exterior surface is substantially planar.

7. The tip part of claim 1, wherein the window comprises a first material and the exterior housing comprises, a second material, the second material different than the first material.

8. The tip part of claim 1, wherein first lens is a wafer lens.

9. The tip part of claim 1, wherein the vision receptor comprises the casing and a lens stack having the first lens and a second lens, the lens stack being positioned inside the casing, the second lens being positioned successively in front of the first lens.

10. The tip part of claim 1, wherein the casing abuts the vision sensor and the first lens.

11. The tip part of claim 1, wherein the vision receptor and/or the tip part do(es) not comprise a separate lens barrel or envelope configured to support the first lens or plurality of lenses.

12. An endoscope, comprising: a tip part according to claim 1.

13. A tip for an endoscope, comprising:
- a vision receptor having a first lens and a vision sensor for providing an image from received light;
- a first light source;
- a housing extending axially from a proximal end to a distal end and having a front wall and an exterior facing side wall, the front wall having an exterior surface and an interior surface opposite the exterior surface, the front wall and the exterior facing side wall defining an interior spacing, the exterior facing side wall connected to and extending proximally from the front wall, the housing made of an opaque material and accommodating the vision sensor and the first light source in the interior spacing;
- a casing extending proximally from the interior surface of the front wall toward the proximal end of the housing, the housing formed in one-piece with the casing and the front wall, and the casing surrounding the first lens; and
- a window comprising a transparent material and positioned at the distal end of the housing axially in front of the vision sensor, the window comprising a light source zone and a vision receptor zone,
- wherein the casing comprises a distal end embedded in the window at least in part between the light source zone and the vision receptor zone to prevent internal reflections in the window from reaching the vision receptor.

14. The tip of claim 13, wherein the window is integrally formed with the housing in a two component moulding process.

15. The tip of claim 13, further comprising a light shield between the vision sensor and the first light source.

16. The tip of claim 13, further comprising a lens barrel, the first lens supported by the lens barrel, the lens barrel bonded inside the casing to secure the first lens to the tip, wherein the vision sensor is positioned at a proximal end of the lens barrel.

17. The tip of claim 16, further comprising a light guide disposed in front of the first light source, wherein the light guide extends proximally from the front wall, and wherein the tip comprises one part including the exterior housing, the casing, and the light guide.

18. The tip part of claim 5, wherein the side wall and the window are integrally formed in one piece in a two component moulding process.

19. The tip part of claim 1, wherein the casing comprises a longitudinal axis and a first cross-sectional profile at a first position along the longitudinal axis and a second cross-sectional profile at a second position along the longitudinal axis, the second position spaced from the first position, and wherein, the front wall comprises a cross-section that is different than at least the second cross-section profile of the casing.

20. The tip part of claim 1, wherein the casing supports the vision receptor and the light source, and the casing is formed in one modular piece.

21. The tip part of claim 1, wherein the window is positioned flush with and surrounded by an exterior surface of the exterior housing.

22. The tip of claim 13, wherein the casing supports the vision receptor and the light source, and the casing is formed in one modular piece.

23. An endoscope, comprising:
- a handle;
- an insertion tube extending from the handle; and
- a tip according to claim 19 supported by the insertion tube.

* * * * *